(12) United States Patent
Grossman et al.

(10) Patent No.: US 12,150,784 B1
(45) Date of Patent: Nov. 26, 2024

(54) REPLACEABLE CARRIER FOR WEARABLE DEVICES

(71) Applicant: Verily Life Sciences LLC, South San Francisco, CA (US)

(72) Inventors: Jonathan Grossman, South San Francisco, CA (US); Pey-Jiun Ko, South San Francisco, CA (US); David Lari, South San Francisco, CA (US); Jon Echt, South San Francisco, CA (US); Xianyan Wang, South San Francisco, CA (US); Arthur Lin, South San Francisco, CA (US)

(73) Assignee: Verily Life Sciences LLC, Dallas, TX (US)

( * ) Notice: Subject to any disclaimer, the term of this patent is extended or adjusted under 35 U.S.C. 154(b) by 658 days.

(21) Appl. No.: 17/370,153

(22) Filed: Jul. 8, 2021

(51) Int. Cl.
  *A61B 5/00* (2006.01)
  *A61B 5/01* (2006.01)
  *A61B 5/08* (2006.01)

(52) U.S. Cl.
  CPC .............. *A61B 5/6832* (2013.01); *A61B 5/01* (2013.01); *A61B 5/08* (2013.01); *A61B 5/6824* (2013.01); *A61B 5/6833* (2013.01)

(58) Field of Classification Search
  None
  See application file for complete search history.

(56) References Cited

U.S. PATENT DOCUMENTS

| | | | |
|---|---|---|---|
| 6,925,317 B1* | 8/2005 | Samuels | A61B 5/6833 600/344 |
| 10,945,668 B2 | 3/2021 | Biederman et al. | |
| 2002/0070447 A1* | 6/2002 | Kinsman | H01L 25/0657 257/723 |
| 2019/0350526 A1* | 11/2019 | Biederman | B65D 83/08 |
| 2020/0011746 A1* | 1/2020 | Allen, Sr. | G01K 13/20 |
| 2020/0367824 A1 | 11/2020 | Frick et al. | |
| 2022/0233144 A1* | 7/2022 | Furneaux | A61B 5/6833 |

\* cited by examiner

*Primary Examiner* — Erica S Lee
(74) *Attorney, Agent, or Firm* — Haynes and Boone, LLP

(57) ABSTRACT

A body-mountable monitoring device includes a sensing device, a carrier body removably coupled to the sensing device, and an adhesive sheet bonded to the carrier body and configured to couple the carrier body to a user's skin, where the carrier body surrounds sidewalls of the sensing device such that at least a top surface is exposed when the sensing device is coupled to the carrier body.

7 Claims, 17 Drawing Sheets

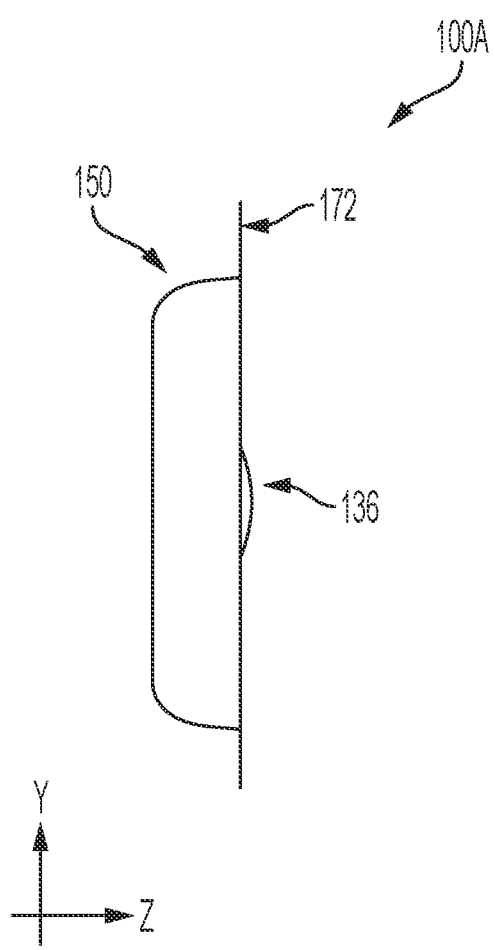
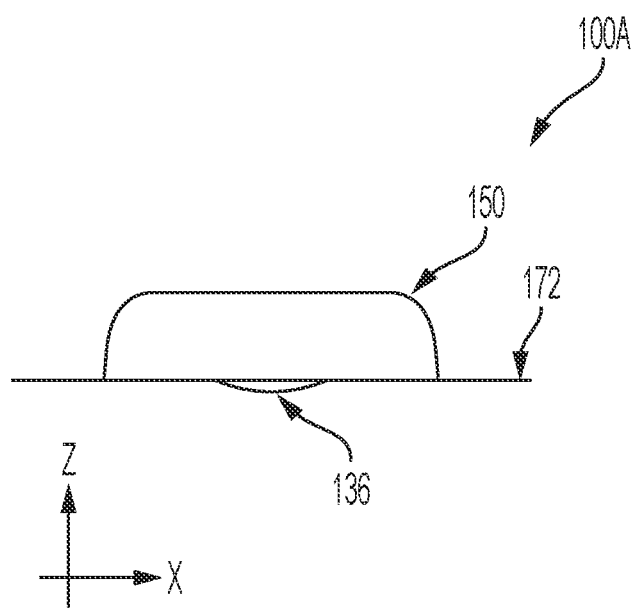
FIG. 3
FIG. 4

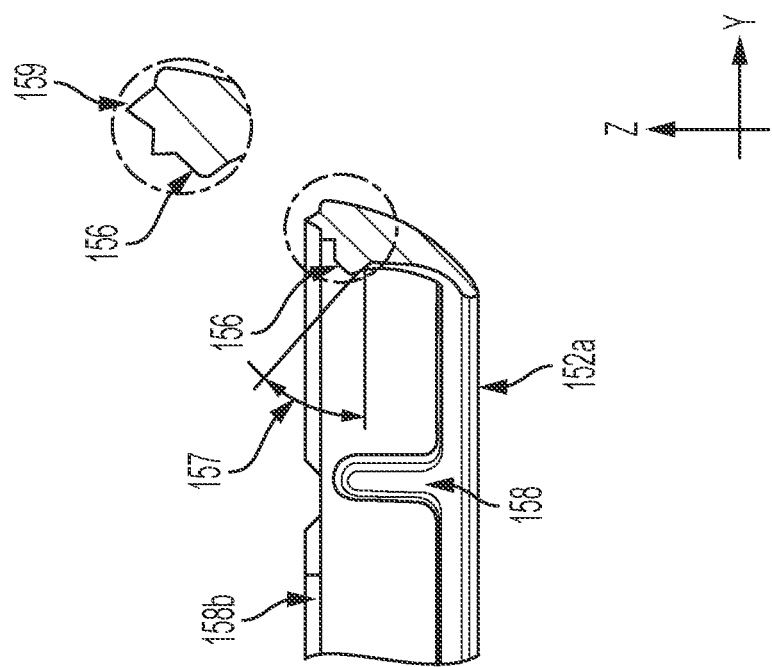
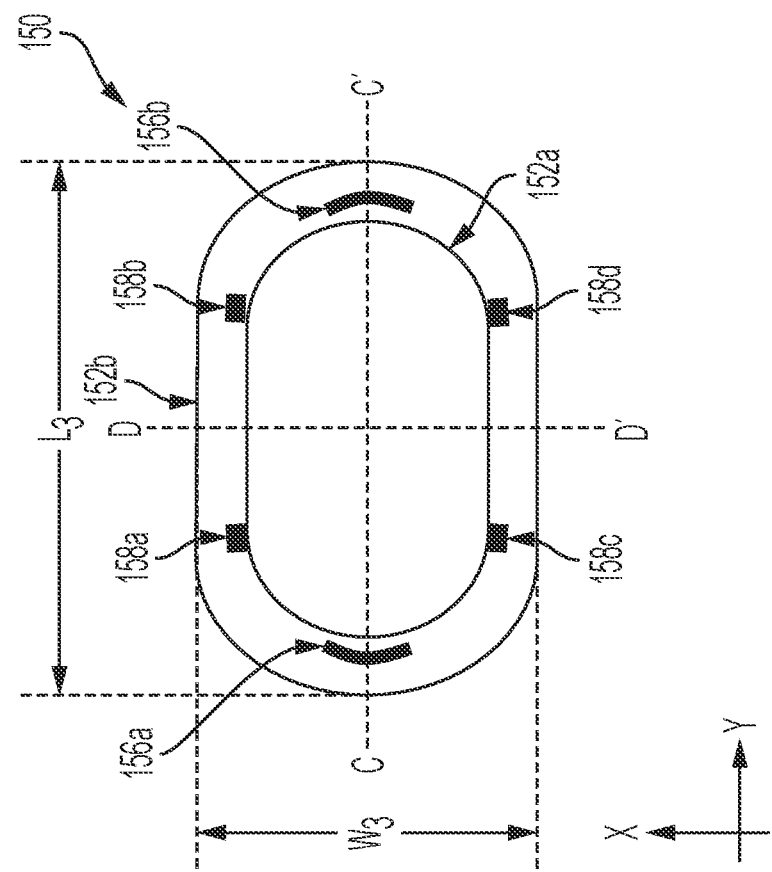
FIG. 11B
FIG. 11A

REPLACEABLE CARRIER FOR WEARABLE DEVICES

TECHNICAL FIELD

The present disclosure relates generally to a replaceable adhesive carrier configured for a body-mountable monitoring device.

BACKGROUND

Body-mountable monitoring (or sensing) devices may be worn on the skin of a user. In some instances, the monitoring devices are worn by the user for multiple days via an adhesive layer that couples to the monitoring device and the skin of the user. Generally, body-mountable monitoring devices may be categorized as disposable or reusable. For a disposable body-mountable monitoring device, both the monitoring device and the adhesive layer are discarded after a period of wearing, such as when the adhesive layer begins to break down. A reusable body-mountable monitoring device, on the other hand, may include a reusable monitoring device and a replaceable adhesive layer. For example, after the adhesive layer starts to fail, a new adhesive layer may be attached to the monitoring device and reapplied to the skin of the user.

While existing implementations of body-mountable monitoring devices have generally been adequate, they are not entirely satisfactory in all aspects. For example, the new adhesive layer may require time and care to apply and may include a complex series of steps for proper application. In addition, designs of some existing body-mountable monitoring devices may introduce discomfort when both the monitoring device and the adhesive layer are in contact with the user's skin.

BRIEF DESCRIPTION OF THE DRAWINGS

Illustrative embodiments of the present disclosure will be described with reference to the accompanying drawings, of which:

FIG. 3 is a planar, side view of the body-mountable monitoring device of FIG. 1, in accordance with at least one embodiment of the present disclosure.

FIG. 4 is a planar, side view of the body-mountable monitoring device of FIG. 1, in accordance with at least one embodiment of the present disclosure.

FIG. 11A is a planar, bottom view of the carrier of FIG. 9, in accordance with at least one embodiment of the present disclosure.

FIG. 11B is a cross-sectional view of the carrier of FIG. 11A along line CC', in accordance with at least one embodiment of the present disclosure.

DETAILED DESCRIPTION

Figure 1:
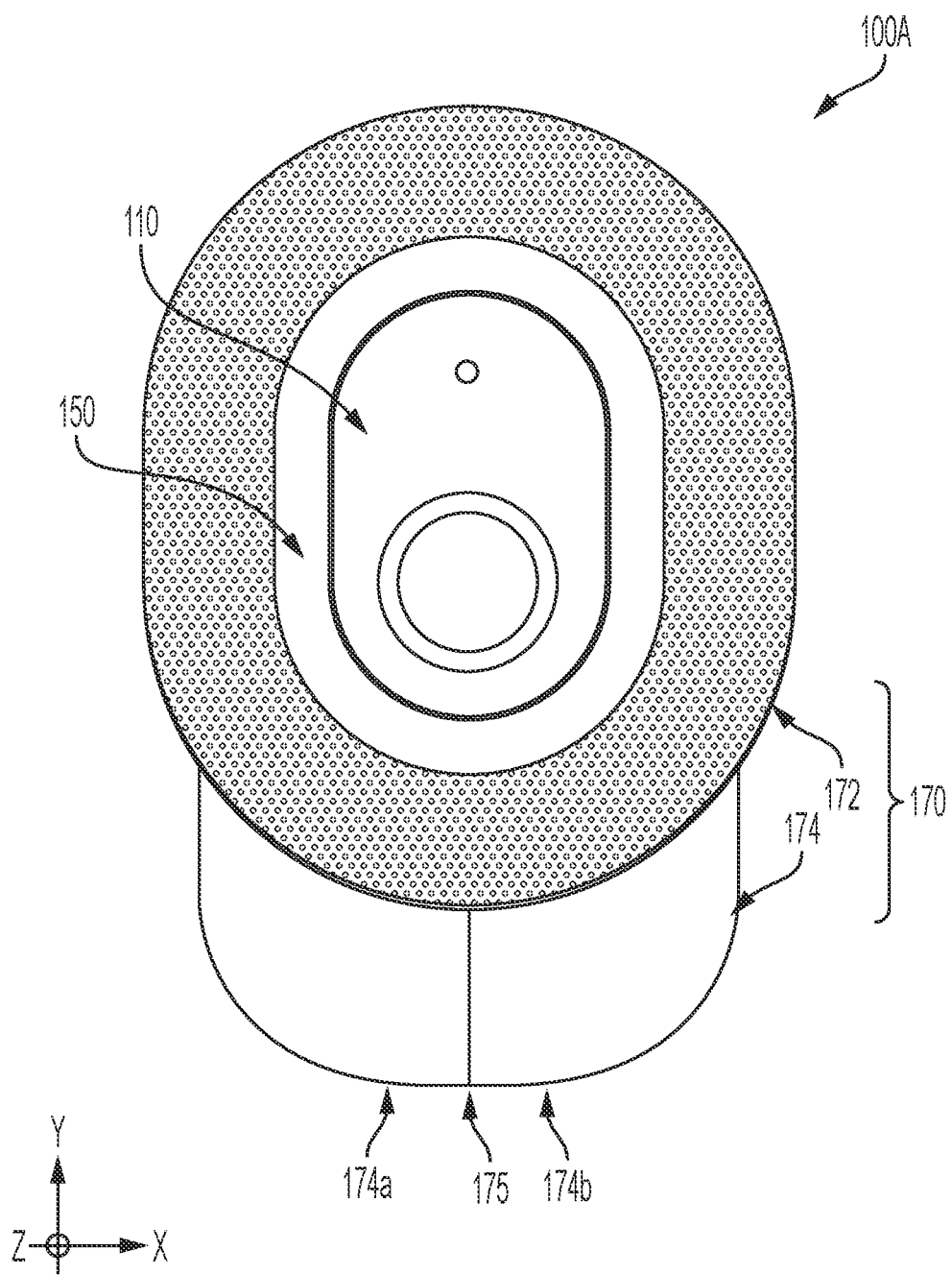
FIG. 1 is a planar, top view of an example body-mountable monitoring device, in accordance with at least one embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Body-mountable monitoring (or sensing) devices are worn on the skin of a user. In some instances, the monitoring devices are worn by the user for multiple days via an adhesive layer that couples to the monitoring device and the skin of the user. For a reusable body-mountable monitoring device, the adhesive layer is discarded periodically (such as when the adhesive layer breaks down and/or loses its adhesiveness), while the monitoring device is reattached to the user via a new adhesive layer. Although existing body-mountable monitoring devices have made tracking biological metrics accessible, many challenges remain with respect to designing and fabricating more user-friendly devices. For example, the new adhesive layer may require time and care to apply, may be difficult to align with the monitoring device, or may include multiple parts that increases complexity during application. In addition, designs of some existing body-mountable monitoring devices may introduce discomfort when both the monitoring device and the adhesive layer are in contact with the user's skin.

The present disclosure provides a body-mountable monitoring device that includes a reusable monitoring device and a removable adhesive carrier that couples the monitoring device with a user's skin. In some embodiments, the adhesive carrier and the monitoring device are configured with complementary features that help the user to identify the correct orientation to assemble the body-mountable monitoring device without needing to perform an extensive alignment process (via an applicator, for example). As such, the user may apply the body-mountable monitoring device by simply peeling off a release liner of the adhesive layer and adhering it to any desired location. In some embodiments, the removable adhesive carrier includes a carrier coupled to the adhesive layer and is configured to hold the monitoring device in place, providing ergonomic features for the user to handle the body-mountable monitoring device during the application process.

In one aspect, the present disclosure provides a body-mountable monitoring device that includes a sensing device, a carrier body removably coupled to the sensing device, and an adhesive sheet bonded to the carrier body and configured to couple the carrier body to a user's skin, where the carrier body surrounds sidewalls of the sensing device such that at least a top surface is exposed when the sensing device is coupled to the carrier body.

In another aspect the present disclosure provides an adhesive carrier that includes a ring-shaped carrier body having a top edge opposite to a bottom edge, an adhesive sheet having an adhesive surface opposite to a non-adhesive surface, and a removable liner attached to the adhesive surface, where the non-adhesive surface is bonded to the bottom edge of the ring-shaped carrier body, and where the removable liner extends beyond a perimeter of the adhesive sheet.

In yet another aspect, the present disclosure provides a method that includes providing a monitoring device, inserting the monitoring device in a first adhesive carrier to form a wearable device, where the first adhesive carrier includes a first carrier body bonded to a first adhesive sheet and a first release liner attached to the first adhesive sheet, and where the monitoring device is enclosed by the first carrier body. The method further includes removing the first release liner to expose the first adhesive sheet, contacting the exposed first adhesive sheet to a region of a user's skin to adhere the wearable device, detaching the first adhesive sheet to remove the wearable device from the region of the user's skin, and subsequently removing the monitoring device from the removed wearable device.

These descriptions are provided for example purposes only and should not be considered to limit the scope of the body-mountable monitoring device. Certain features may be added, removed, or modified without departing from the spirit of the claimed subject matter.

Figure 2:
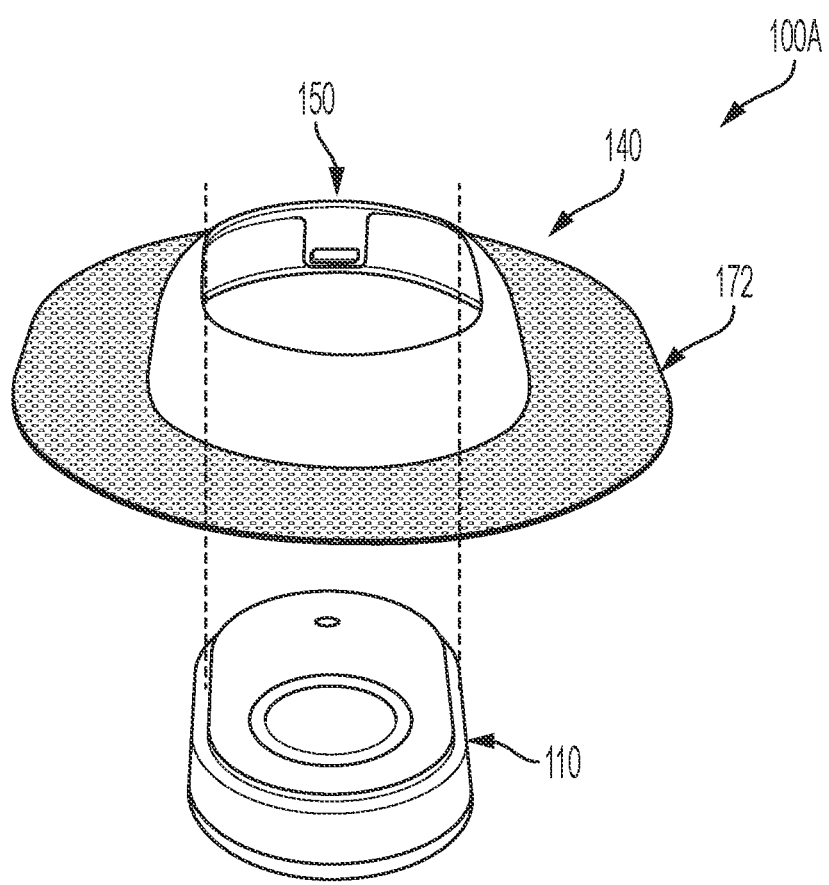
FIG. 2 is a perspective, exploded view of the body-mountable monitoring device of FIG. 1, in accordance with at least one embodiment of the present disclosure.

FIGS. 1-4 illustrate an example body-mountable monitoring device (alternatively referred to as a wearable device or a wearable patch) 100A in accordance with at least one embodiment of the present disclosure. FIG. 1 depicts a planar top view of the body-mountable monitoring device 100A being oriented widthwise along the X axis and lengthwise along the Y axis with its thickness protruding along the Z axis; FIG. 2 is an exploded, perspective view of the body-mountable monitoring device 100A; and FIGS. 3 and 4 depict side views of the body-mountable monitoring device 100A in the planes YZ and XZ, respectively.

In the present embodiments, the body-mountable monitoring device 100A is a patch-like, wearable sensor that can be attached directly to a user's skin via a removable adhesive carrier. In some embodiments, the body-mountable monitoring device 100A is configured to monitor a user's body temperature, respiratory rate, other biological metrics, or combinations thereof. In some embodiments, the body-mountable monitoring device 100A is adhered to the skin of the user's underarm region (e.g., in or near the armpit).

Referring to FIGS. 1 and 2, the body-mountable monitoring device 100A includes a monitoring device (or sensing device) 110 nested in an opening of an adhesive carrier 140, where the adhesive carrier 140 further includes a carrier body 150 bonded to an adhesive assembly 170. As discussed in detail below, structures of the body-mountable monitoring device 100A are configured to allow the user to insert the monitoring device 110 in an adhesive carrier 140 to assemble the body-mountable monitoring device 100A, attach the assembled body-mountable monitoring device 100A to a desired region of the user's skin via the adhesive assembly 170, remove the assembled body-mountable monitoring device 100A from the user's skin after a period of time, separate the monitoring device 110 from the used adhesive carrier 140, and discard the used adhesive carrier 140. The monitoring device 110 may then be reattached to the user after being coupled to a new adhesive carrier 140. Such application and re-application processes may be repeated numerous times.

In the present embodiments, the adhesive assembly 170 includes an adhesive sheet 172 attached to a release liner 174, where opening of the carrier body 150 is aligned with an opening of the adhesive sheet 172 to form the opening of the adhesive carrier 140. In the present embodiments, the carrier body 150 (or a bottom edge thereof) is bonded to the adhesive sheet 172, such that the monitoring device 110 is coupled to the entirety of the adhesive carrier 140. Furthermore, the adhesive sheet 172 extends outwardly beyond a perimeter (or footprint) of the carrier body 150 to provide sufficient surface area for attaching the adhesive carrier 140 to the skin of the user. In other words, a ring-shaped footprint of the adhesive sheet 172 occupies a larger area than the perimeter of the carrier body 150.

After removing the release liner 174, portions of the adhesive sheet 172 that extend away from the bottom edge of the carrier body 150 adhere to the user's skin. After a period of wearing (which may be determined based on a material used in the adhesive sheet 172, for example), the body-mountable monitoring device 100A may be removed from the skin by removing the adhesive sheet 172, and the used adhesive carrier 140 may be discarded and replaced with a new adhesive carrier 140.

In some embodiments, as depicted in FIG. 1, portions of the release liner 174 include tabs 174a and 174b split along a cut line 175 and extending away from the bottom edge of the adhesive sheet 172. In other words, a footprint of the tabs 174a and 174b extend beyond the footprint of the adhesive sheet 172. The extended and split tabs 174a and 174b allow the user to grasp the release liner 174 and separate the release liner 174 from the adhesive sheet 172. It is noted that other suitable configurations of the release liner 174 not depicted herein may also be applicable in the present disclosure.

Referring to FIGS. 3 and 4, the monitoring device 110 is nested in the opening of the carrier body 150 with a top surface of the monitoring device 110 being coplanar or substantially coplanar with a top edge of the carrier body 150. In other words, a top surface of the body-mountable monitoring device 100A is substantially flat or smooth across the transition from the top surface of the monitoring device 110 to the outer surface of the carrier body 150. Because the top surface of the body-mountable monitoring device 100A may also be in contact with the user's skin (for example, when the body-mountable monitoring device 100A is applied to the underarm region), maintaining a substantially flat or smooth top surface may help reduce discomfort associated with wearing the device, thereby improving user experience for long-term application. In the present embodiments, a thermal contact 136 of the monitoring device 110 protrudes from a bottom surface of the carrier body 150 to contact the user's skin upon application. In some embodiments, the thermal contact 136 is a metal contact configured with a convex profile protruding away from the adhesive sheet 172. In other words, the thermal contact 136 forms a recessed structure in the bottom surface of the carrier body 150.

Figure 5:
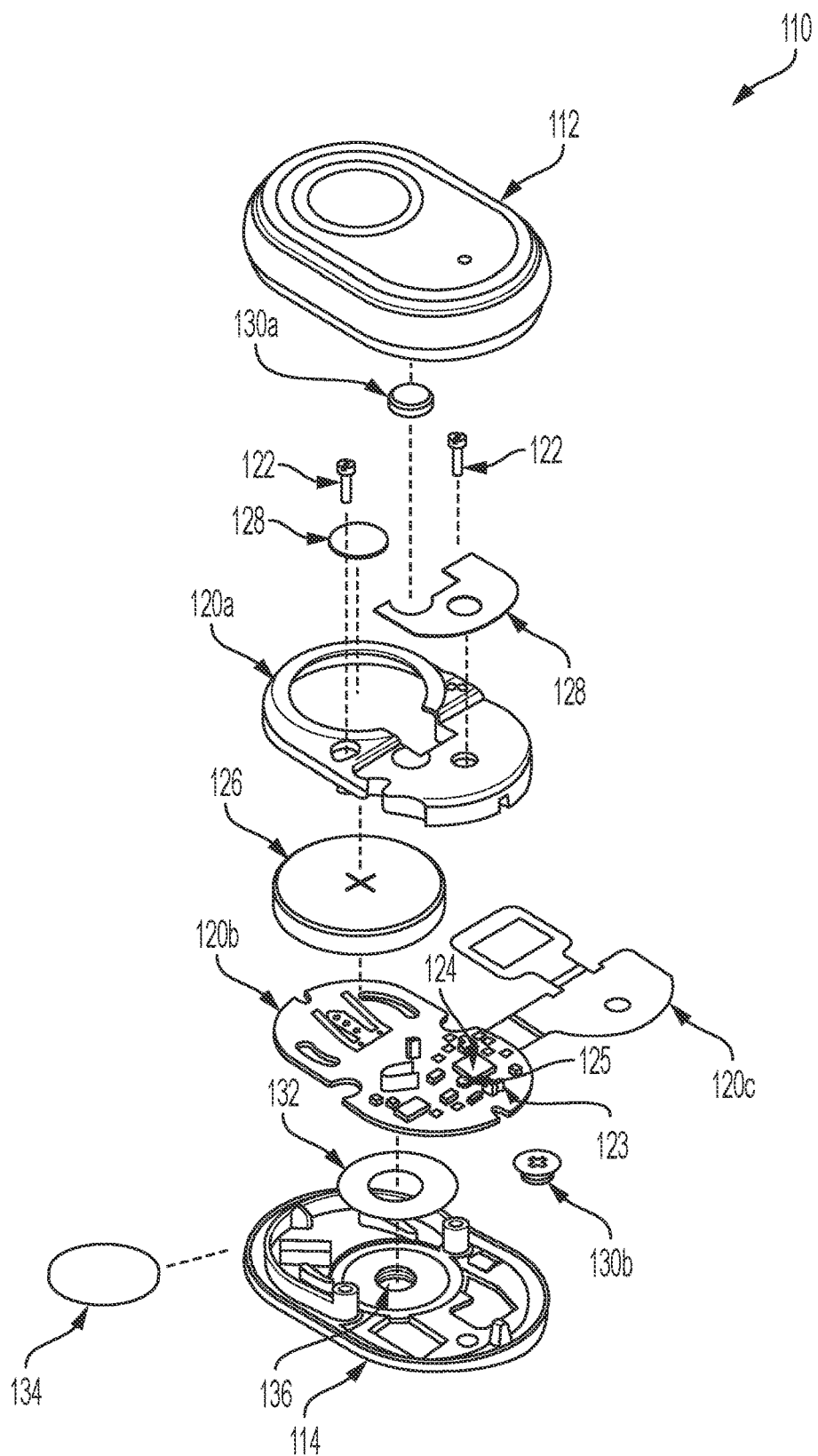
FIG. 5 is a perspective, exploded view of a monitoring device of the example body-mountable monitoring device of FIG. 1, in accordance with at least one embodiment of the present disclosure.
Figure 6:
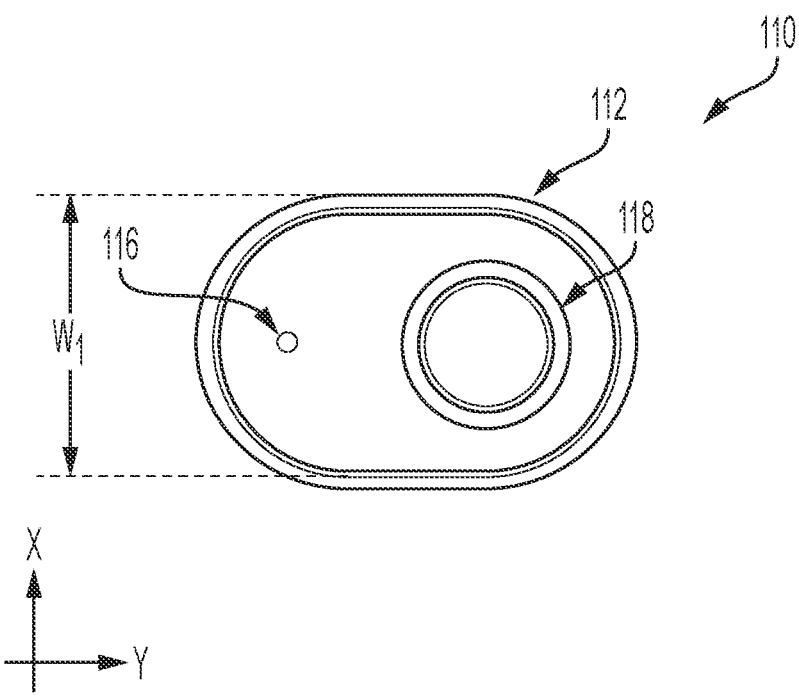
FIG. 6 is a planar, top view of the monitoring device of FIG. 5, in accordance with at least one embodiment of the present disclosure.
Figure 7:
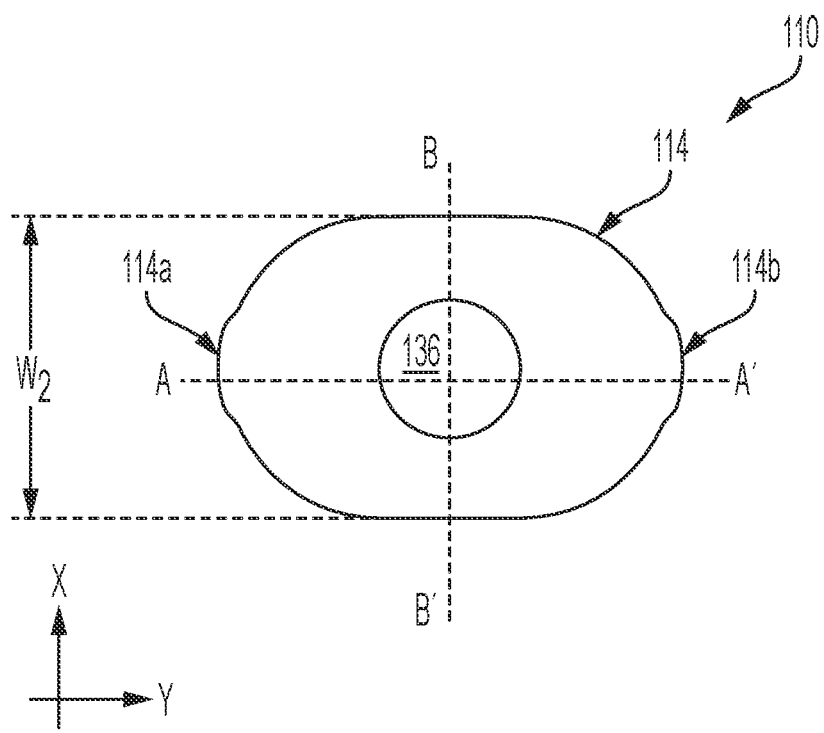
FIG. 7 is a planar, bottom view of the monitoring device of FIG. 5, in accordance with at least one embodiment of the present disclosure.

FIGS. 5-7 illustrate an example embodiment of the monitoring device 110 and various components thereof. In some embodiments, the monitoring device 110 is configured to monitor metrics, including body temperature and respiratory rate, associated with common illnesses. It is noted the monitoring device 110 may also be configured to monitor other symptoms not discussed herein.

Referring to FIG. 5, the monitoring device 110 includes an upper housing 112 and a complementary lower housing 114 coupled to the upper housing 112. In some embodiments, both the upper housing 112 and the lower housing 114 comprise a thermoplastic resin. In an example embodiment, the thermoplastic resin includes a polyester-based copolymer. Other suitable materials may also be suitable for fabricating the upper housing 112 and the lower housing 114. In some embodiments, the upper housing 112 and the lower housing 114 are configured with different colors for ease of identification by the user.

The monitoring device 110 generally includes a support frame having a cover 120a disposed over a substrate 120b and a flexible cover 120c extended from and attached to the substrate 120b. In the depicted embodiments, the cover 120a is coupled to the lower housing 114 by two fasteners (such as screws) 122, sandwiching the substrate 120b therebetween. In some embodiments, the substrate 120b is a printed circuit board (PCB). The substrate 120b includes an accelerometer 123 in communication with a microcontroller 124, which may include a processor and a memory (not depicted separately). In the present embodiments, the accelerometer 123 is configured to detect a user's respiratory rate.

The monitoring device 110 further includes a temperature sensor (not depicted in FIG. 5) in communication with the microcontroller 124. The temperature sensor may be a thermistor, a resistance temperature detector (RTD), a capacitance temperature sensor, a semiconductor device, or an infrared camera. In some embodiments, the temperature sensor is disposed under the substrate 120b and within a recess of the thermal contact 136. In the present embodiments, the temperature sensor is coupled with the thermal contact 136 (see FIGS. 3, 4, and 7), which protrudes from the lower housing 114. In some embodiments, the thermal contact 136 is a metal component integrated with the lower housing 114. In some embodiments, the monitoring device 110 further includes a port cover 134 configured to cover an opening in a portion of the lower housing 114 offset from the thermal contact 136.

In some embodiments, the microcontroller 124 is configured for wireless communication with a remote device via a network. In some embodiments, the remote device is a smart phone, tablet computer, personal digital assistant (PDA), or personal computing device (PCDs), other suitable devices, or combinations thereof. In some embodiments, the network includes the Internet, one or more local area networks, a Bluetooth low-energy network, one or more wide area networks, one or more cellular networks, one or more wireless networks, one or more voice networks, one or more data networks, one or more communication systems, or combinations thereof.

In the present embodiments, the substrate 120b further includes a light-emitting diode (LED) 125 in communication with at least the microcontroller 124. The LED 125 illuminates through a translucent region 116 (shown in FIG. 6) of the upper housing 112 to signal to the user the status of various operations of the monitoring device 110. It is noted that the arrangement of the accelerometer 123, the temperature sensor, the microcontroller 124, and the LED 125 on the substrate 120b is not limited in the present disclosure and may be configured according to specific design considerations.

In some embodiments, the support frame further encloses a power supply 126 disposed over the substrate 120b and in communication with the accelerometer 123, the temperature sensor, the microcontroller 124, and the LED 125. In some embodiments, the power supply 126 includes a battery and/or other suitable power source.

After fastening the cover 120a to the lower housing 114 by the screws 122, the flexible cover 120c is folded over the power supply 126 and a portion of the cover 120a. In some embodiments, pressure-sensitive adhesive (PSA) sheets 128 are configured with suitable shapes to adhere the flexible cover 120c to the cover 120a.

The monitoring device 110 may include additional features to accommodate the assembly of the support frame and the various components disposed therein. For example, the monitoring device 110 may include thermal paste 130a and 130b configured to isolate various thermal components from their surrounding environment, thereby preventing inadvertent heat exchange and ensuring accurate temperature monitoring. Additionally, the monitoring device 110 may include a PSA seal 132 that provides sealing for a gap between the thermal contact 136 and the lower housing 114 to prevent ingress of external elements, such as water leak. Additional or fewer components may be possible in the assembly of the monitoring device 110.

Referring to FIG. 6, which depicts a planar top view of the monitoring device 110, the upper housing 112 includes at least the translucent region 116 configured to show light illuminated by the LED 125 and a button 118 configured to provide the user with the means to operate the monitoring device 110. In the present embodiments, the button 118 is in communication with the microcontroller 124, such that depressing the button 118 turns on/off the monitoring device 110. Depressing the button 118 may also instruct the monitoring device 110 to perform one or more additional operations. In some embodiments, the button 118 comprises an elastomeric material, which may differ from the more rigid structure of the upper housing 112. In some embodiments, the button 118 is configured with a concave profile is lower than the top surface of the upper housing 112, allowing the user to identify the location of the button 118 even when the body-mountable monitoring device 100A is out of sight (for example, when the body-mountable monitoring device is attached to the underarm region). In an example embodiment, a width W1 of the upper housing 112 is about 21.052±0.075 mm.

Referring to FIG. 7, which depicts a planar bottom view of the monitoring device 110, line AA' diagrammatically defines a centerline across the lower housing 114 along the Y axis and line BB' diagrammatically defines a centerline across the lower housing 114 along the X axis. In the present disclosure, the lines AA' and BB' are alternatively termed the major axis and the minor axis, respectively, of the lower housing 114. In this regard, the lower housing 114 includes protrusions 114a and 114b on opposite ends of the carrier body 150 along line AA', while such protrusions are absent along the line BB'. Furthermore, referring to FIG. 6 for comparison, the upper housing 112 does not include any such protrusion along its perimeter. In other words, the protrusions 114a and 114b are asymmetrically positioned on the lower housing 114 with respect to the upper housing 112. In the present embodiments, the protrusions 114a and 114b are configured to assist the user to distinguish the lower housing 114 (the bottom surface) from the upper housing 112 (the top surface), such that the user could correctly install the monitoring device 110 in the adhesive carrier 140 with the upper housing 112 facing upward in the opening of the carrier body 150. In some embodiments, the protrusions 114a and 114b serve as tactile markers for the user to identify the correct orientation for inserting the monitoring device 110 into the carrier body 150. In further embodiments, the protrusions 114a and 114b are configured to prevent improper insertion of the monitoring device 110 into the carrier body 150 (e.g., the monitoring device 110 being inserted in an incorrect orientation), which ensures the data collected by the monitoring device 110 are accurate. In an example embodiment, a width W2 of the lower housing 114 measured along is substantially the same as the width W1 of the upper housing and is about 21.052±0.075 mm.

Figure 8:
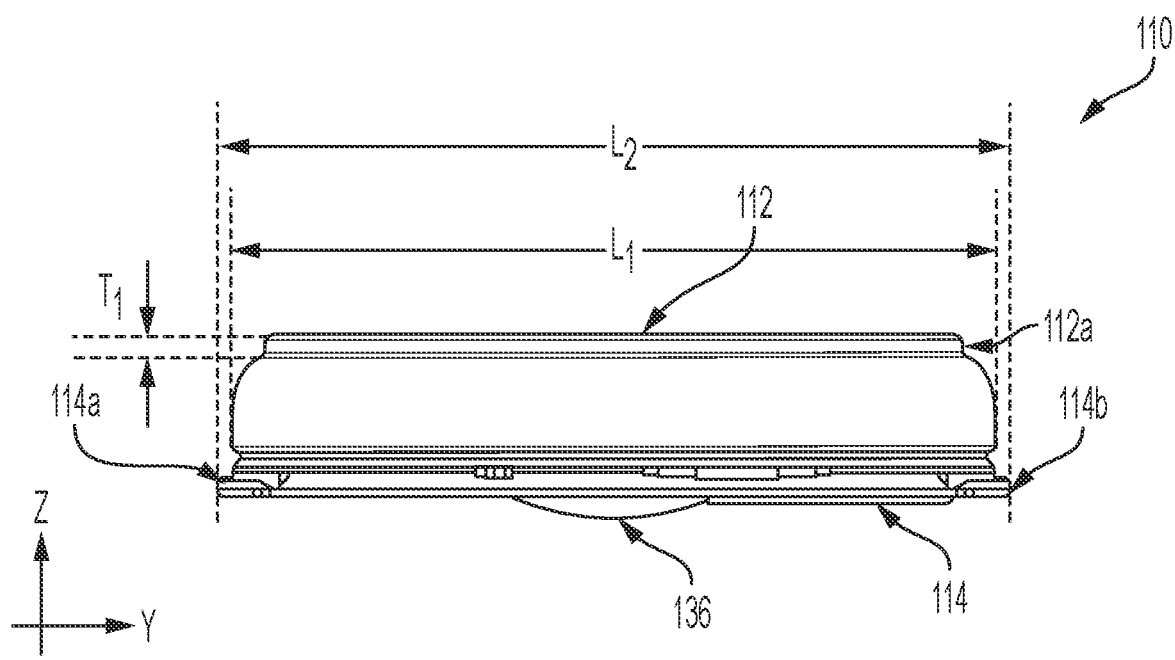
FIG. 8 is a planar, side view of the monitoring device of FIG. 5, in accordance with at least one embodiment of the present disclosure.

Referring to FIG. 8, which depicts a side view of the monitoring device 110, the upper housing 112 includes a raised edge 112a. In the present embodiments, the raised edge 112a protrudes from an underlying portion of the upper housing 112 by a height $T_1$, which is consistent with a thickness of the carrier body 150 along its top edge 152a (shown in FIG. 9, for example). For example, in some embodiments, the height $T_1$ is equal or approximately equal (+/−5%) to thickness of the carrier body 150 at the top edge 152a. After the monitoring device 110 is placed in the carrier body 150, the complementary fitting between the raised edge 112a and the top edge 152a of the carrier body 150 forms a continuous, curved boundary or profile around the top surface of the body-mountable monitoring device 100A, leading to a substantially smooth top surface and therefore a more comfortable wearing experience for the user. This may be particularly beneficial when the top surface of the body-mountable monitoring device 100A is in direct contact with the user's skin, such as when the body-mountable monitoring device 100A is placed in the user's underarm region. In an example embodiment, a length $L_1$ of the upper housing 112 and a length $L_2$ of the lower housing 114, each measured along the line AA', are about 31.05 mm and about 32.223±0.075 mm, respectively.

FIGS. 9-11B illustrate the carrier body 150 from various perspectives. In some embodiments, the carrier body 150 comprises a rigid, thermoplastic resin configured to provide structural support for the monitoring device 110. In some embodiments, the same material implemented for the fabrication of the upper housing 112 and the lower housing 114 is also implemented for the fabrication of the carrier body 150. In an example embodiment, the carrier body 150 includes a polyester-based copolymer. Other suitable materials may also be contemplated for fabricating the carrier body 150. For example, the carrier body 150 may comprise a flexible silicone-based material.

Figure 10:
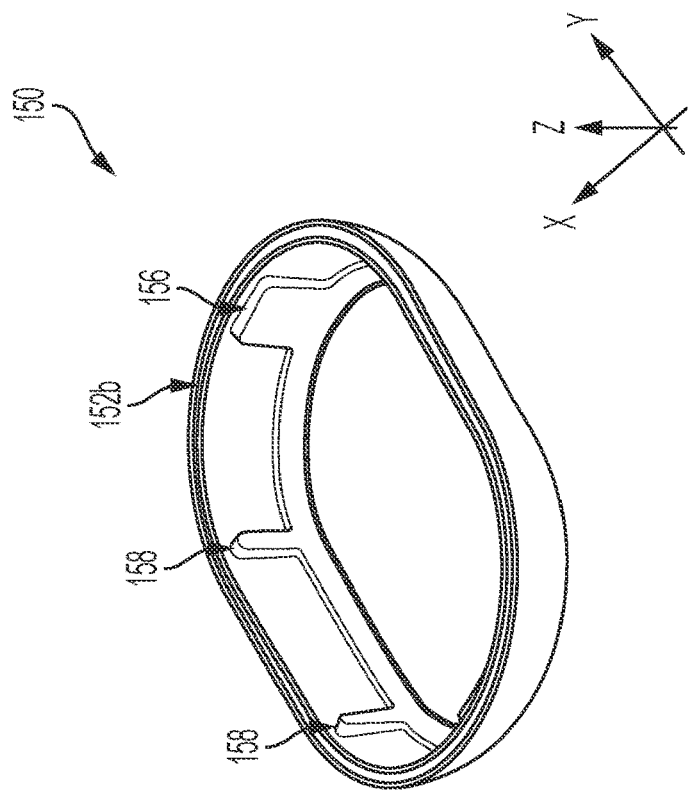
FIG. 10 is a perspective, bottom view of the carrier body of FIG. 9, in accordance with at least one embodiment of the present disclosure.
Figure 9:
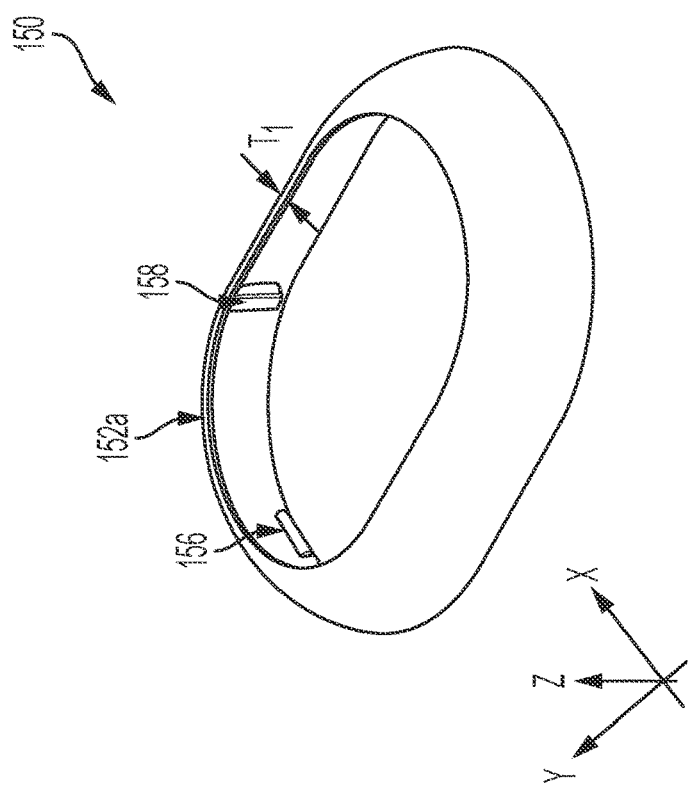
FIG. 9 is a perspective, top view of a portion of a carrier body of the example body-mountable monitoring device of FIG. 1, in accordance with at least one embodiment of the present disclosure.

In an example embodiment, referring to FIG. 9, which is a perspective top view of the carrier body 150, an external surface of the carrier body 150 is free of any mold release marks to eliminate uneven ridges that may cause discomfort to the user. In the present embodiments, the top edge 152a of the carrier body 150 is formed to a thickness $T_1$ that is consistent with the height of the raised edge 112a as shown in FIG. 8, such that when the monitoring device 110 is secured in the carrier body 150, the top surface of the upper housing 112 connects with the top edge 152a to form a continuous, curved surface. Furthermore, the fitting between the top edge 152a and the raised edge 112a prevents the monitoring device 110 from sliding through the opening formed by the top edge 152a and disengaging with the carrier body 150. In the present embodiments, the opening formed by the top edge 152a is complementary to an area of the top surface of the upper housing 112 that fully exposes the translucent region 116 and the button 118. By comparison, the opening formed by a bottom edge 152b opposite to the top edge 152a as shown in FIG. 10 is larger than the opening formed by the top edge 152a to expose an entirety or at least a majority of a bottom planar surface area of the lower housing 114, as well as to accommodate the bonding between the carrier body 150 and the adhesive assembly 170 discussed in detail below.

In some embodiments, the openings formed by the top edge 152a and the bottom edge 152b conform to a shape of the monitoring device 110, which may be determined based on various design considerations and are thus not limited to any specific configurations in the present disclosure. In some embodiments, the monitoring device 110 is a ring-shaped structure, where the openings formed by the top edge 152a and the bottom edge 152b are each configured as a circular, elliptical, rectangle with rounded corners, square with rounded corners, stadium, or other suitable shape. In the depicted embodiments, the openings formed by the top edge 152a and the bottom edge 152b are each configured as an elongated shape, such as an elliptical or a stadium shape, that may be defined by a major axis and a minor axis perpendicular to the major axis.

In some embodiments, the carrier body 150 includes features designed to securely confine the monitoring device 110 in place. Referring to FIGS. 10 and 11A, which depict a bottom portion of the carrier body 150 in a perspective view and a planar view, respectively, an interior surface of the carrier body 150 includes two opposing stabilizers 156 (such as 156a and 156b shown in FIG. 11A). In the present embodiments, the stabilizers 156a-156b are positioned symmetrically, or substantially symmetrically, on opposite ends of the carrier body 150 along line CC', which diagrammatically defines a centerline across the carrier body 150 along the Y axis. In the present disclosure, the line CC' is alternatively termed the major axis of the carrier body 150. In some embodiments, each stabilizer 156 is configured as a bar-shaped, raised structure with a length that conforms to a curvature of the carrier body 150. In some embodiments, referring to FIG. 11B, which is a cross-sectional view of FIG. 11A along the line CC', each stabilizer 156 is positioned at an angle 157 with respect to the top edge 152a, where the angle 157 is an acute angle. In an example embodiment, the angle 157 is about 42°. In the present embodiments, the stabilizers 156a and 156b are designed to secure the monitoring device 110 in place after being inserted into the carrier body 150. Specifically, the raised and angled profile of the stabilizers 156 is configured to clamp the monitoring device 110 from opposite ends by engaging within the recess formed between the upper housing 112 and the lower housing 114 of the monitoring device 110, thereby preventing the monitoring device 110 from becoming loosened from the carrier body 150y while being worn by the user. In addition, the design and the position of the stabilizers 156 allow the monitoring device 110 to be easily removed from the carrier body 150 when the user desires to replace the adhesive carrier 140.

Furthermore, the interior surface of the carrier body 150 includes a plurality of ribbing structures 158 (such as 158a, 158b, 158c, and 158d shown in FIG. 11A) disposed between the stabilizers 156. In the present embodiments, the ribbing structures 158 are configured to provide separation between the carrier body 150 and the monitoring device 110 created by a bonding interface between the carrier body 150 and the adhesive sheet 172 as discussed in detail below.

In some embodiments, the carrier body 150 includes four ribbing structures 158 with two of the ribbing structures 158 (such as 158a and 158b or 158c and 158d) being positioned along each long edge of the carrier body 150. Each of the ribbing structures 158 extends from the top edge 152a to the bottom edge 152b along the interior surface of the carrier body 150. In some embodiments, a separation distance between two adjacent ribbing structures 158 is configured to accommodate the placement of a product identification number (such as lot number). In some embodiments, the ribbing structures 158 are positioned symmetrically, or substantially symmetrically, about both the line CC' and line DD', which diagrammatically defines a centerline across the carrier body 150 along the X axis and is alternatively termed the minor axis of the carrier body 150. For example, the ribbing structures 158a and 158b are symmetrically positioned about the line DD', the ribbing structures 158a and 158c are symmetrically positioned about the line CC', the ribbing structures 158c and 158d are symmetrically positioned about the line DD', and the ribbing structures 158b and 158d are symmetrically positioned about the line CC'. Depending upon specific design considerations, more or less of the ribbing structures 158 may be implemented and their relative positions may also be altered.

In an example embodiment, referring to FIG. 11A, a length $L_3$ of the carrier body 150 measured along the line CC' is about 35.98 mm and a width W3 of the carrier body 150 measured along the line DD' is about 25.98 mm.

Figure 12:
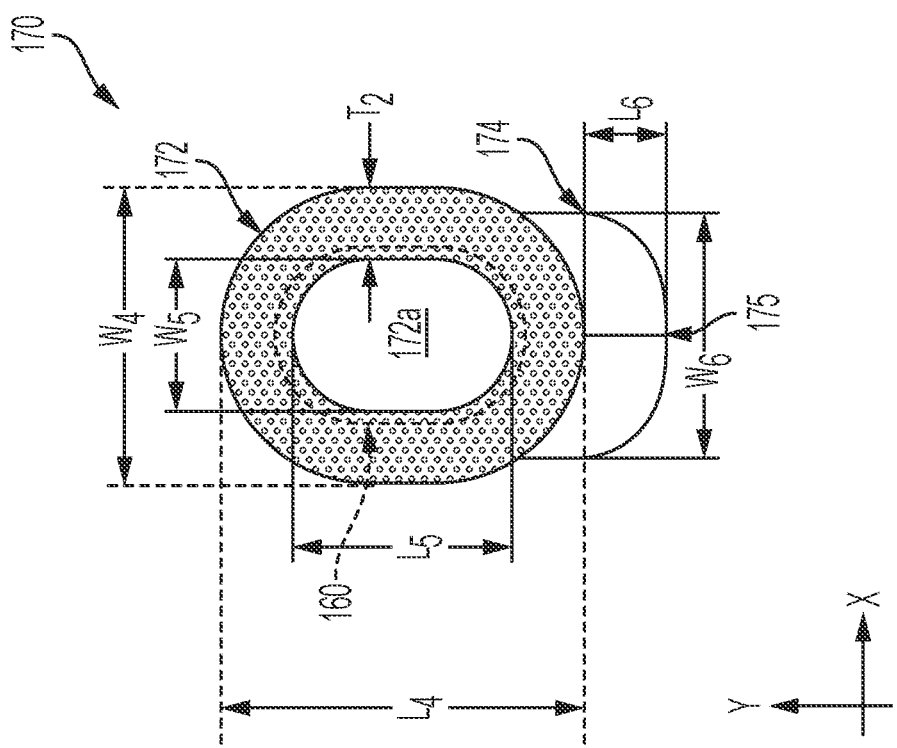
FIG. 12 is a planar, top view of an adhesive assembly of the example body-mountable monitoring device of FIG. 1, in accordance with at least one embodiment of the present disclosure.

FIG. 12 illustrates a planar top view of the adhesive assembly 170, which includes the adhesive sheet 172 attached to the release liner 174. In the present embodiments, the adhesive sheet 172 is single-sided adhesive sheet having an adhesive layer lined by a non-adhesive backing layer on the top (the shaded region) and attached to the release liner 174 on the bottom (shown in both FIGS. 12 and 13).

In some embodiments, the non-adhesive backing layer includes a spunlace nonwoven material, such as polyester, and the adhesive layer includes a skin adhesive material, such as an acrylic-based pressure-sensitive material. In some embodiments, the adhesive layer includes a skin-friendly adhesive material. In one such example, the adhesive sheet 172 may be a DermaMed DM-2001C medical adhesive. Other suitable non-adhesive backing materials and medical-grade adhesive materials may also be applicable in the present embodiments. For example, the adhesive layer may include a silicone-based adhesive, a natural or synthetic rubber-based adhesive, a hydrogel-based adhesive, a hydrocolloid-based adhesive, a polyurethane-based adhesive, other suitable materials, or combinations thereof. In some embodiments, the adhesive layer is selected to minimize occurrence of the adhesive layer adhering to itself contacting the user's skin. Because the non-adhesive backing layer is bonded to the carrier body 150 by a suitable bonding process such as heat welding, ultrasonic bonding, solvent bonding, adhesive bonding, and/or plasma bonding, the non-adhesive backing material may be selected to accommodate such bonding process.

In some embodiments, the adhesive layer includes an adhesive material having properties permitting it to be peeled from the user's skin by pulling a corner or edge from the skin without damaging the skin. In some embodiments, the adhesive material is selected to retain its adhesive property in the presence of a body fluid, such as sweat, that may be secreted while the body-mountable monitoring device 100A is worn by the user. In some embodiments, to ensure complete removal of the adhesive sheet 172 without, or substantially without, any residue remaining on the user's skin, a solvent-containing removing wipe may be applied to the non-adhesive backing layer to dissolve the adhesive layer before removing the adhesive sheet 172 from the user's skin. In some embodiments, the adhesive material is selected to be removable without the use of water, soap, solvent, or other releasing material.

Figure 13:
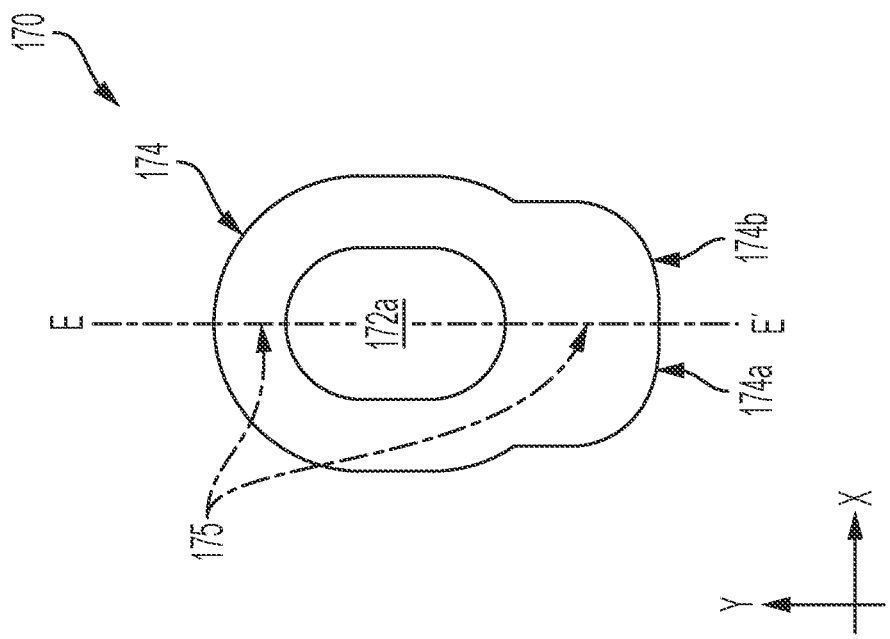
FIG. 13 is a planar, bottom view of the adhesive assembly of FIG. 12, in accordance with at least one embodiment of the present disclosure.
Figure 15:
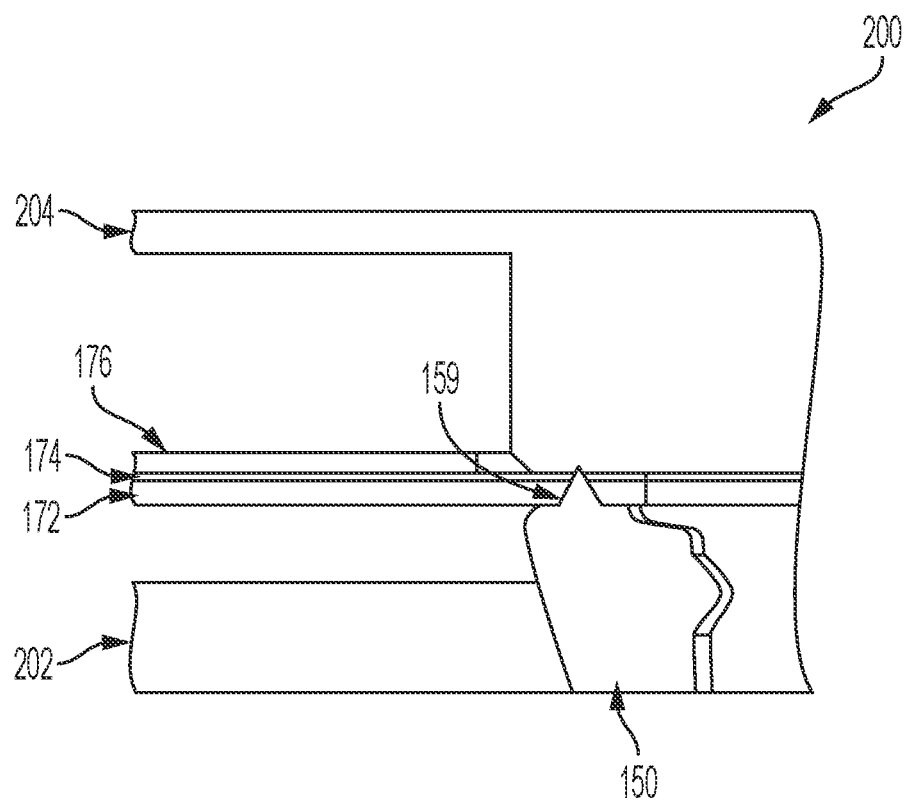
FIG. 15 is a cross-sectional view of an example heat bonding apparatus configured to form the adhesive carrier of FIG. 14, in accordance with at least one embodiment of the present disclosure.

Referring to FIGS. 12 and 13, the release liner 174 includes a top portion that conforms to the configuration of the adhesive sheet 172 and a bottom portion that extends away from the adhesive sheet 172. In the present embodiments, the bottom portion of the release liner 174 is configured as two tabs 174a and 174b split along a cut line 175. As depicted herein, the cut line 175 extends vertically along the Y axis from the top portion to the bottom portion of the release liner 174. In some embodiments, the cut line 175 coincides with a diagrammatic centerline EE' of the release liner 174. In the present embodiments, the cut line 175 allows the user to remove the release liner 174 by separating the tabs 174a and 174b. In this regard, the release liner 174 may be removed one portion at a time, where each portion requires less pulling force to be removed than if the release liner 174 were to be removed in its entirety. In addition, the cut line 175 allows the user to easily separate the release liner 174 from the adhesive sheet 172, making the adhesive assembly 170 more user-friendly. In some embodiments, an alignment liner 176 (shown in FIG. 15) is attached to the release liner 174 and is configured to provide alignment between the adhesive assembly 170 and the carrier body 150 during a heat bonding process that joins the two components together.

In some embodiments, the adhesive assembly 170 optionally includes a secondary release liner (not depicted) disposed over and removably adhered to the non-adhesive backing layer of the adhesive sheet 172. This secondary release liner may be configured to extend from the perimeter of the adhesive sheet 172, thereby providing additional footprint to allow the user to handle the adhesive carrier 140. In some examples, the secondary release liner may be at least the same size as the release liner 174. In addition, the secondary release liner may provide additional structural support for the adhesive sheet 172 to prevent any inadvertent fold-over after the release liner 174 is removed. In some embodiments, the secondary release liner comprises a more rigid material than the release liner 174. After the assembled body-mountable monitoring device 100A is applied to a desired region of the skin, the secondary release liner can be removed from the adhesive sheet 172.

In an example embodiment, referring to FIG. 12, a length $L_4$ and a width $W_4$ of the adhesive sheet 172 are about 53.91 mm and about 43.91 mm, respectively; a length $L_5$ and a width $W_5$ of an opening 172a of the adhesive sheet 172 are about 32.48 mm and 22.48 mm, respectively; and a length $L_6$ and a width W6 of the portion of the release liner 174 that extends beyond the bottom portion of the adhesive sheet 172 are about 12 mm and about 36 mm, respectively. Furthermore, a width $T_2$ of the adhesive sheet 172 measured around the opening 172a is about 10 mm.

Figure 14:
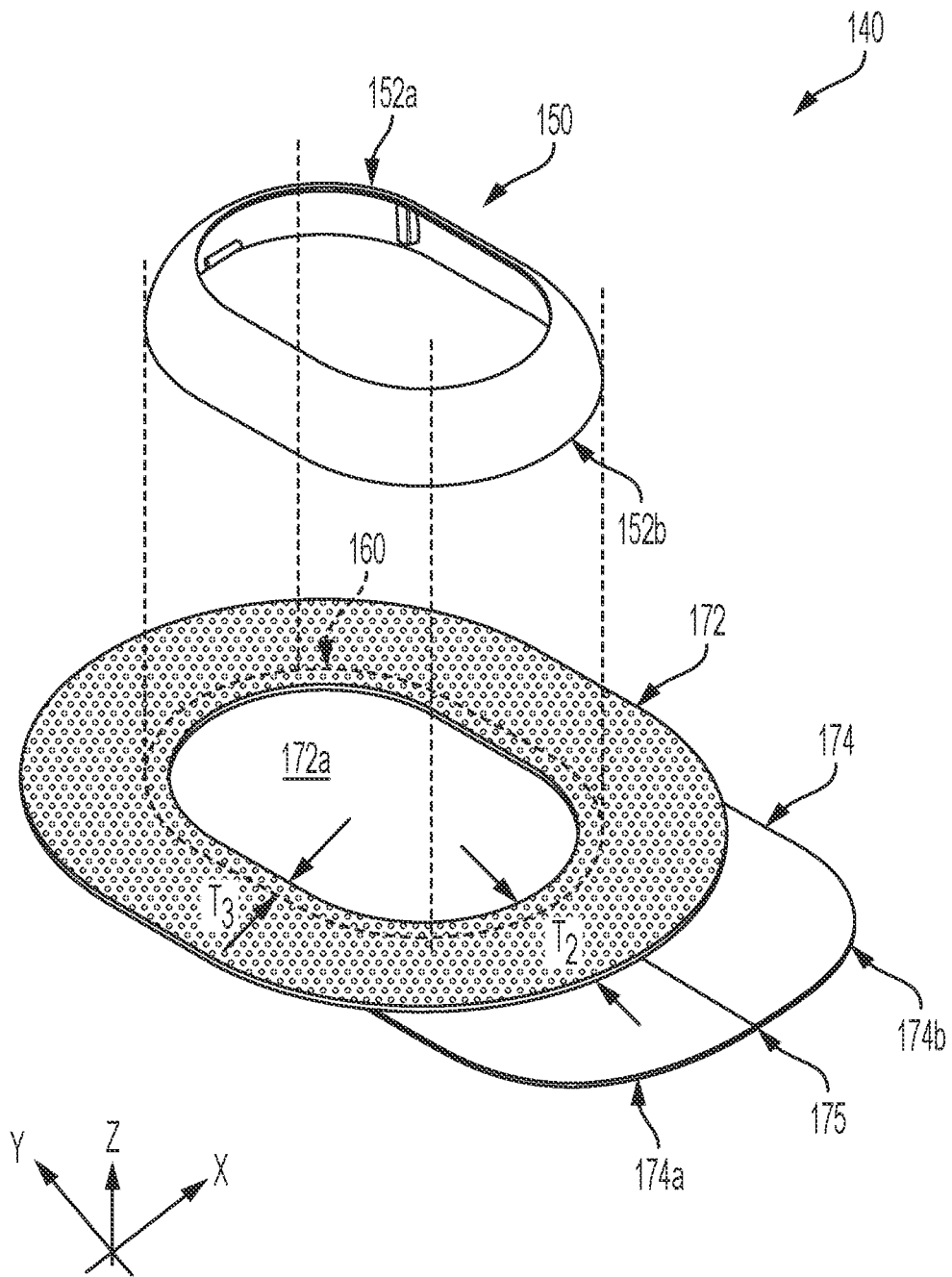
FIG. 14 is a perspective, exploded view of an adhesive carrier, including the carrier body of FIG. 9 bonded to the adhesive assembly of FIG. 12, of the example body-mountable monitoring device of FIG. 1, in accordance with at least one embodiment of the present disclosure.

FIG. 14 is an exploded, perspective view of the adhesive carrier 140 depicting the interface 160 between the carrier body 150 and the non-adhesive backing layer of the adhesive sheet 172. In the present embodiments, the bottom edge 152b of the carrier body 150 generally defines a bonding interface 160 (outlined by the dashed curve) between the carrier body 150 and the adhesive sheet 172. To provide enough allowance for the carrier body 150 to bond to the adhesive sheet 172, the opening formed by the bottom edge 152b is larger than the opening 172a of the adhesive sheet 172 (also the opening of the release liner 174), such that the bonding interface 160 encircles the opening 172a. In an example embodiment, an offset $T_3$ between a perimeter of the opening 172a and the interface 160 is about 1.75 mm. For reference, the width $T_2$ of the adhesive sheet 172 may be about 10 mm.

The present disclosure provides various embodiments in which the carrier body 150 may be bonded to the non-adhesive backing layer of the adhesive sheet 172. In some embodiments, as depicted herein, the carrier body 150 is bonded to the adhesive sheet 172 by a heat bonding process. In this regard, the heat bonding process melts both the non-adhesive backing layer of the adhesive sheet 172 and portions of the carrier body 150 around the bottom edge 152b to create a welded connection. In some embodiments, referring to FIG. 15, which depicts an example heat bonding apparatus 200, performing the heat bonding process includes positioning the carrier body 150 with the bottom edge 152b facing upward in a fixture 202, applying the adhesive assembly 170 over the carrier body 150 with the release liner 174 facing upward, and pressing a thermal probe 204 to the release liner 174 through the alignment liner 176, resulting in portions of the non-adhesive backing layer of the adhesive sheet 172 to melt with the carrier body 150 at the interface 160. After the heat bonding process is completed, the alignment liner 176 is removed from the release liner 174, leaving behind the adhesive assembly 170. It is noted that the alignment liner is not a part of the body-mountable monitoring device 100A that requires handling from the user during application. In some embodiments, the heat bonding process is adjusted by controlling time, temperature, and pressure to achieve a desired bond strength that prevents slippage or delamination between the carrier body 150 and the adhesive assembly 170.

In some embodiments, referring to FIG. 11B, the carrier body 150 is molded to include a plurality of energy directors 159 protruding from the bottom edge 152b. The energy directors 159, which are generally triangular, raised features, are configured to make the initial contact with adhesive sheet 172 by deforming the non-adhesive backing layer upon contact and to shape the melted portions of the carrier body 150 into the non-adhesive backing layer of the adhesive sheet 172. In this regard, the melting of the energy directors 159 joins together the carrier body 150 and the non-adhesive backing layer to form the interface 160. As the energy directors 159 melt and integrate with the adhesive sheet 172, some lateral spreading or flow of the melted material(s) may be present near the interface 160. Such lateral spreading may reduce the size of the opening formed by the bottom edge 152b and interfere with the insertion of the monitoring device 110. Accordingly, the ribbing structures 158 located along the interior surface of the carrier body 150 are configured to account for such spreading by providing separation between the carrier body 150 and the monitoring device 110. In addition, the placement of the ribbing structures 158 provides adjustment for the fitting between the carrier body 150 and the monitoring device 110 without needing to increase the thickness of the carrier body 150.

In some embodiments, the degree of protrusion of the ribbing structures 158 from the interior surface of the carrier body 150 is configured to provide allowance for the spreading of the material during the heat bonding process (i.e., the melting of the non-adhesive backing layer and of the carrier body 150, as well as the flow of the adhesive layer), which may be determined based on the locations and geometry of the energy directors 159. In this regard, because the spreading of the melted material is concentrated around the interface 160, the degree of protrusion of the ribbing structures 158 near the bottom edge 152b is greater than the degree of protrusion near the top edge 152a. In some embodiments, the opening formed by the bottom edge 152b is configured to be larger than that formed by the top edge 152a to accommodate the increased degree of protrusion of the ribbing structures 158.

In an example embodiment, as shown in FIG. 11B, one energy director 159 is located above each stabilizer 156 on opposite ends of the carrier body 150 along the line CC', and two additional energy directors 159 (not depicted herein) may each be located between the stabilizers 156 along the bottom edge 152b and symmetric about the line CC'. In some embodiments, separation between two adjacent energy directors 159 is configured to provide a path for moisture (arising from, for example, sweat) to escape from the user, providing relief from skin irritation and potentially extending the wearing period of the body-mountable monitoring device 100A.

Other bonding methods may also be applicable to join the carrier body 150 to the adhesive sheet 172. In one example, an adhesive may be applied to bond the carrier body 150 to the non-adhesive backing layer of the adhesive sheet 172. In another example, portions of the adhesive sheet 172 may be wrapped around and adhered to the interior surface of the carrier body 150. In yet another example, a solvent may be applied to dissolve portions of the carrier body 150 and/or the adhesive sheet 172, and the dissolved portions may then be cured (or otherwise solidified) to form a bonded connection at the interface 160. In some embodiments, the material used in the non-adhesive backing layer is selected based on the bonding method intended for joining the carrier body 150 to the adhesive sheet 172. In an example embodiment, a spunlace nonwoven polyester for the non-adhesive backing material and a polyester-based copolymer for the carrier body 150 are employed for implementing the heat bonding process as discussed above.

In some embodiments, when bonded together, the carrier body 150 helps prevent the adhesive sheet 172 from adhering to itself after the release liner 174 is removed. In addition, the carrier body 150, being a rigid, raised structure, allows the user to easily grasp and handle the body-mountable monitoring device 100A during the application process. This may be especially advantageous if the region of the skin for such application is difficult to reach (such as the underarm region) and/or if the user experiences limited range of mobility for handling the body-mountable monitoring device 100A. Furthermore, because the carrier body 150 is bonded to and aligned with the adhesive sheet 172, the user does not need to perform additional alignment procedures to couple the monitoring device 110 with the adhesive carrier 140, making the assembly of the body-mountable monitoring device 100A more user-friendly.

Figure 16:
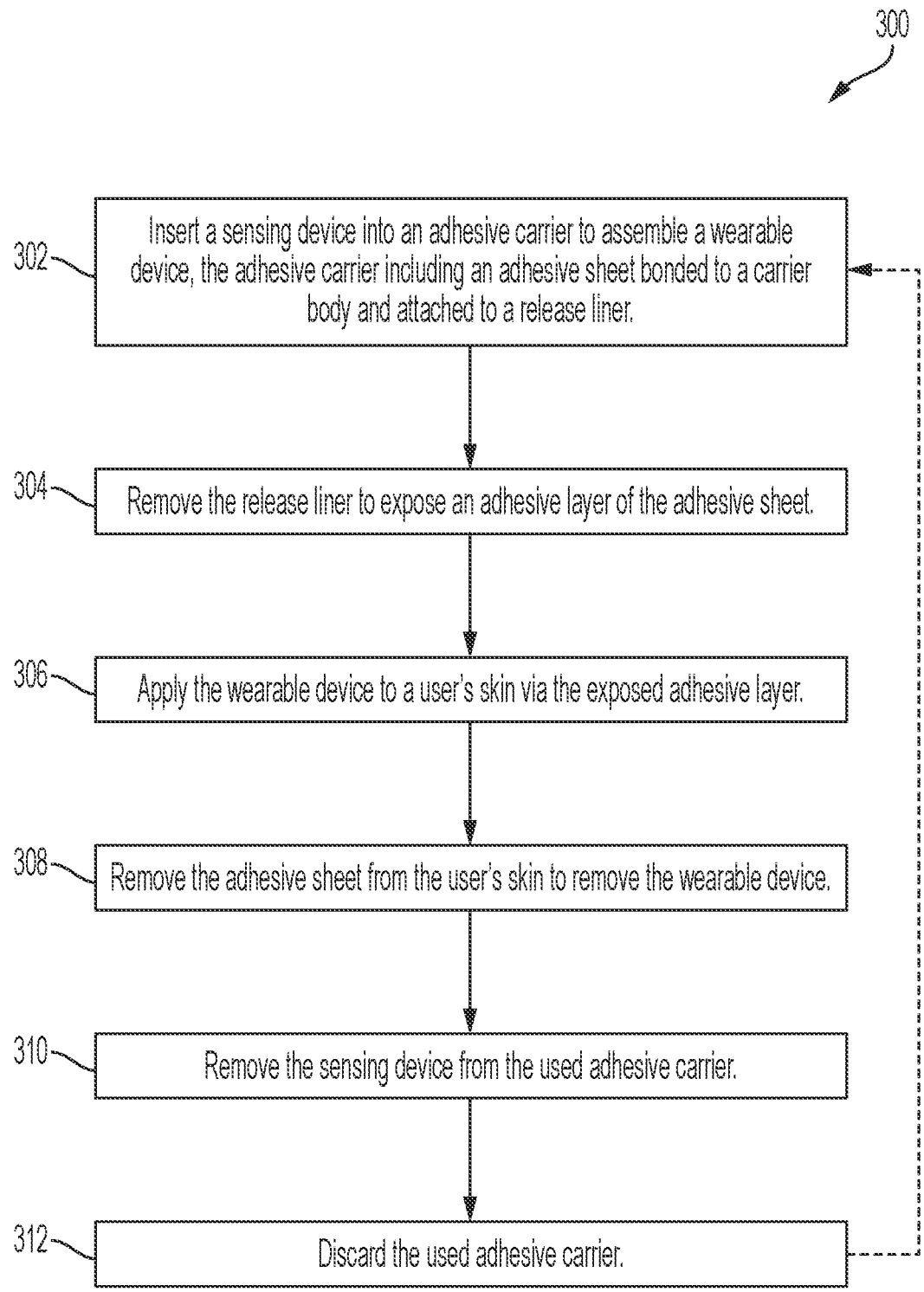
FIG. 16 illustrates an example method of using the body-mountable monitoring device of FIG. 1, in accordance with at least one embodiment of the present disclosure.

In the present embodiments, the adhesive carrier 140, which can be attached and removed from the monitoring device 110, permits the body-mountable monitoring device 100A to be used repeatedly without replacing the monitoring device 110. In this regard, referring to FIG. 16, a method 300 of using the body-mountable monitoring device 100A may include inserting the monitoring device 110 into an adhesive carrier 140 at operation 302, removing the release liner 174 to expose the adhesive layer of the adhesive sheet 172 at operation 304, and applying the body-mountable monitoring device 100A with the exposed adhesive layer in contact with a desired region of the user's skin at operation 306. Subsequently, the method 300 further includes removing the body-mountable monitoring device 100A from the user's skin by removing the adhesive sheet 172 after a predetermined period of wearing at operation 308, removing the monitoring device 110 from the used adhesive carrier 140 at operation 310, discarding the used adhesive carrier 140 at operation 312, and repeating the process of applying the body-mountable monitoring device 100A to the skin as provided in operations 302-306.

Figure 17:
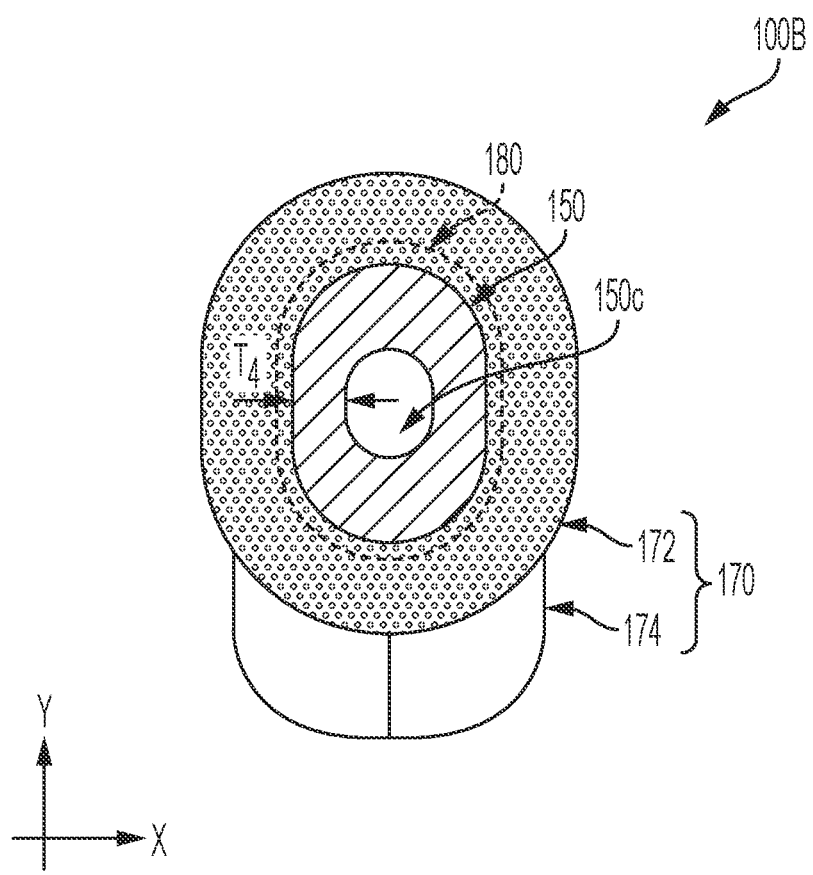
FIG. 17 is a planar, top view of an example body-mountable monitoring device, in accordance with at least one embodiment of the present disclosure.
Figure 18:
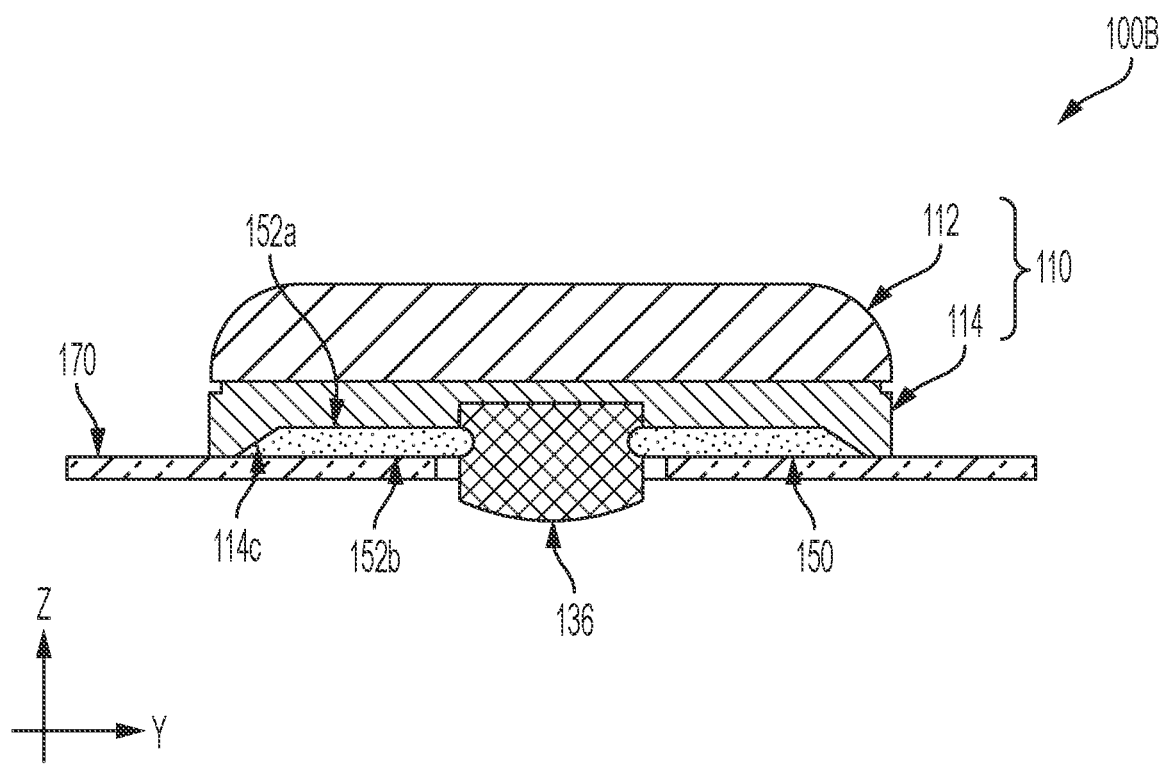
FIG. 18 is a cross-sectional view of the example body-mountable monitoring device of FIG. 17, in accordance with at least one embodiment of the present disclosure.

In some embodiments, referring to FIGS. 17 and 18, the present disclosure provides another body-mountable monitoring device 100B. As illustrated in FIG. 17, the body-mountable monitoring device 100B is similar to the body-mountable monitoring device 100A in that the body-mountable monitoring device 100B includes the monitoring device 110 attached to the adhesive carrier 140, where the adhesive carrier 140 includes the carrier body 150 bonded to the adhesive assembly 170, which further includes the adhesive sheet 172 removably adhered to the release liner 174. However, further referring to FIG. 18, which is a cross-sectional view of the body-mountable monitoring device 100B in the plane YZ, the body-mountable monitoring device 100B differs from the body-mountable monitoring device 100A in that the carrier body 150 is disposed under, rather than surrounding, the monitoring device 110. In other words, the monitoring device 110 covers an entirety (i.e., both the top edge 152a and the bottom edge 152b) of the carrier body 150 in the assembled body-mountable monitoring device 100B, such that a perimeter 180 of the monitoring device 110 surrounds the carrier body 150 as shown in FIG. 17.

In the depicted embodiments, the carrier body 150 is a ring-shaped structure having an opening 150c that allows the thermal contact 136 to protrude through and contact the user's skin. Additionally, referring to FIG. 18, the lower housing 114 of the monitoring device 110 may include a recess 114c that conforms to the configuration of the carrier body 150. In this regard, assembling the body-mountable monitoring device 100B includes coupling the lower housing 114 to the carrier body 150, such that the thermal contact 136 extends through the opening 150c. In some embodiments, as depicted in FIG. 18, to ensure secure attachment to the monitoring device 110, the opening 150c is configured to be slightly smaller than a diameter of the thermal contact 136. In alternative embodiments, the thermal contact 136 includes grooves (not depicted) along its perimeter configured to securely couple with the opening 150c once the body-mountable monitoring device 100B is assembled. As such, the recess 114c may be eliminated from the lower housing 114.

Figure 19:
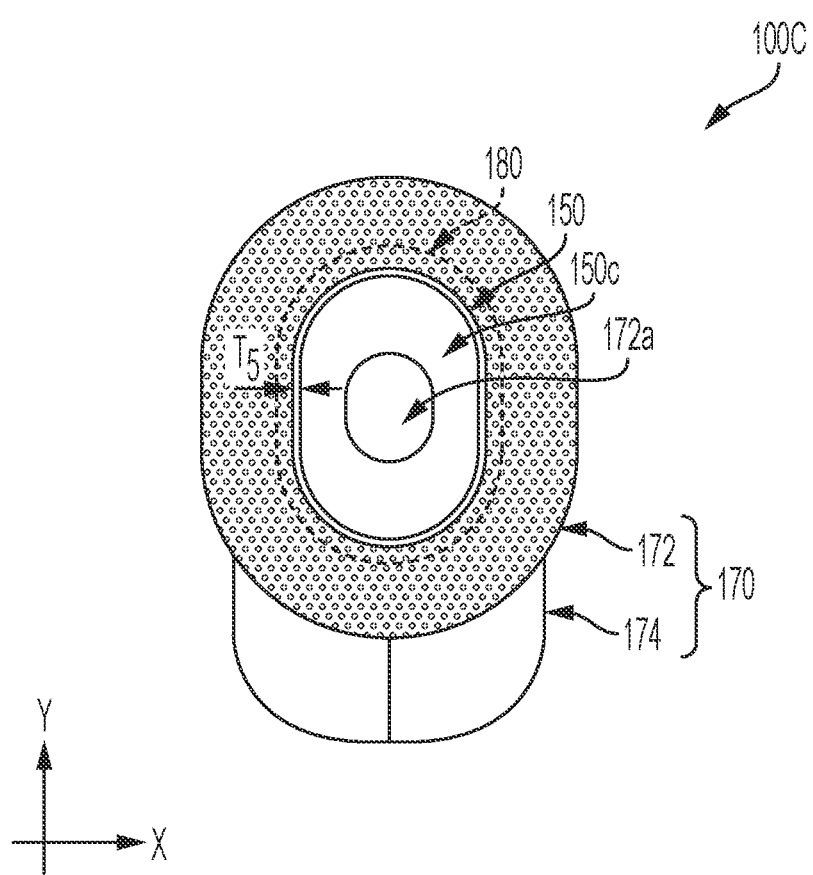
FIG. 19 is a planar, top view of an example body-mountable monitoring device, in accordance with at least one embodiment of the present disclosure.
Figure 20:
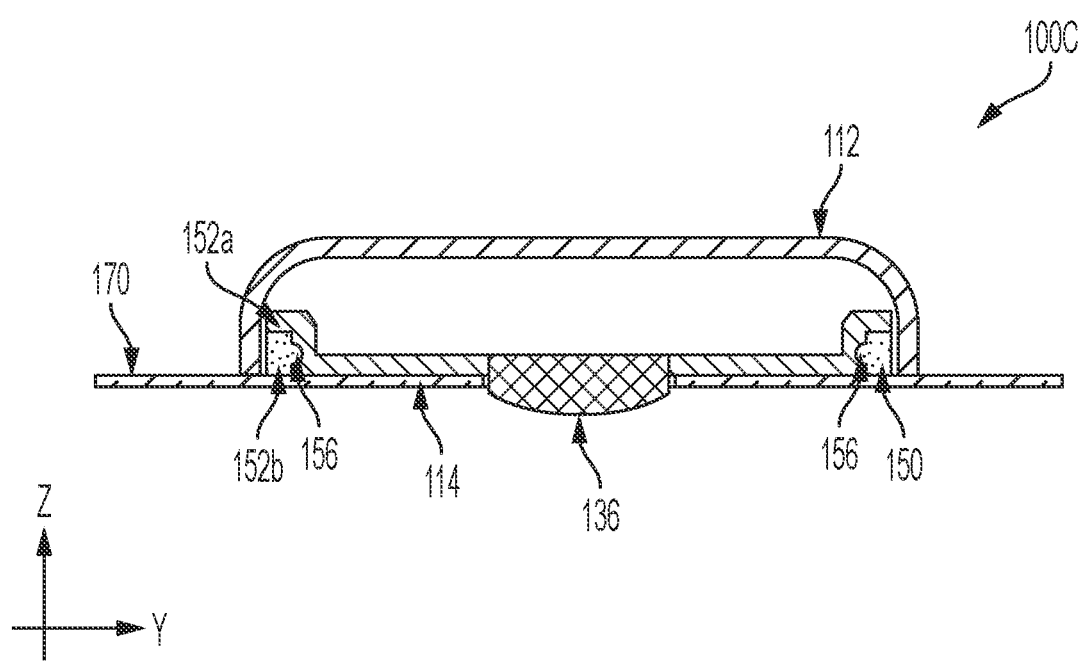
FIG. 20 is a cross-sectional view of the example body-mountable monitoring device of FIG. 19, in accordance with at least one embodiment of the present disclosure.

In some embodiments, referring to FIGS. 19 and 20, the present disclosure further provides a body-mountable monitoring device 100C. The body-mountable monitoring device 100C is similar to the body-mountable monitoring device 100B in that an entirety (i.e., both the top edge 152a and the bottom edge 152b) of the carrier body 150, which is also a ring-shaped structure, is disposed under the monitoring device 110, such that the perimeter 180 of the monitoring device 110 surrounds the carrier body 150. However, the body-mountable monitoring device 100C differs from the body-mountable monitoring device 100B in that a width $T_5$ of the carrier body 150 of the body-mountable monitoring device 100C is less than a width $T_4$ of the carrier body 150 of the body-mountable monitoring device 110B, where both the widths $T_4$ and $T_5$ are measured in their respective planar top views. In the present embodiments, referring to FIG. 19, the opening 150c of the carrier body 150 surrounds the opening 172a of the adhesive sheet 172, which allows the thermal contact 136 to penetrate through and contact the user's skin.

In some embodiments, referring to FIG. 20, the body-mountable monitoring device 100C further differs from the body-mountable monitoring device 100B (and 100A) in that the upper housing 112 of the monitoring device 110 is coupled to the lower housing 114 on an inside surface of a sidewall of the upper housing 112, rather than in a clam-shell configuration. In other words, the sidewall of the upper housing 112 extends over and surrounds a sidewall of the lower housing 114.

Furthermore, as depicted herein, the sidewall of the lower housing 114 is configured to couple with the stabilizers 156 of the carrier body 150, which is similar to the stabilizers 156 discussed above with respect to the body-mountable monitoring device 100A. In the present embodiments, each stabilizer 156 of the body-mountable monitoring device 100C is configured to engage with a portion of the monitoring device 110, i.e., the upper housing 112 or the lower housing 114. In some embodiments, the stabilizer 156 is a continuous, ring-shaped structure along a perimeter of the carrier body 150. In alternative embodiments, the stabilizer 156 includes multiple, discontinuous portions (similar to the stabilizers 156a and 156b of the body-mountable monitoring device 100A) that are distributed along the perimeter of the carrier body 150. It is noted that both the body-mountable monitoring devices 100B and 110C are assembled by applying the monitoring device 110 over the carrier body 150, whereas the assembly of the body-mountable monitoring device 100A is implemented by applying the carrier body 150 over the monitoring device 110.

Figure 21:
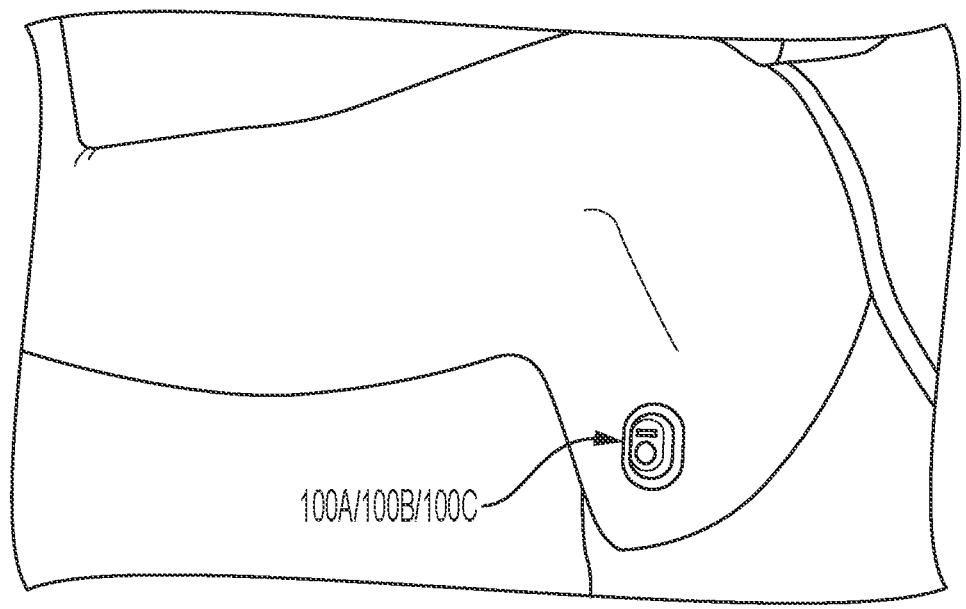
FIG. 21 illustrates the example body-mountable monitoring device of FIG. 1, 17, or 19 being worn in an underarm area of a user.

Example embodiments disclosed herein are directed to the body-mountable monitoring device 100A/100B/100C as being configured to monitor biological metrics, such as body temperature and/or respiratory rate when applied in an underarm region of the user's skin (referring to FIG. 21 for example). Other applications of the body-mountable monitoring device 100A/100B/100C may also be contemplated. For example, the present embodiments may be applied in compliance monitoring for substance abuse treatment programs. Additionally, the present embodiments may be applied to body-mountable monitoring devices that monitor other metrics and/or substance levels in and/or through the skin. Alternatively, or additionally, the body-mountable monitoring device 100A/100B/100C may perform useful functions such as motion tracking, communication, or display of health data or other information. Alternatively, the present embodiments may be applied to non-electronic devices such as passive drug delivery patches, recreational stickers, or other passive devices, without departing from the spirit or subject matter of the present disclosure.

A number of variations are possible on the examples and embodiments described above. Accordingly, the logical operations making up the embodiments of the technology described herein are referred to variously as operations, steps, objects, elements, components, layers, modules, or otherwise. Furthermore, it should be understood that these may occur in any order, unless explicitly claimed otherwise or a specific order is inherently necessitated by the claim language.

Generally, any creation, storage, processing, and/or exchange of user data associated with the method, apparatus, and/or system disclosed herein is configured to comply with a variety of privacy settings and security protocols and prevailing data regulations, consistent with treating confidentiality and integrity of user data as an important matter. For example, the apparatus and/or the system may include a module that implements information security controls to comply with a number of standards and/or other agreements. In some embodiments, the module receives a privacy setting selection from the user and implements controls to comply with the selected privacy setting. In some embodiments, the module identifies data that is considered sensitive, encrypts data according to any appropriate and well-known method in the art, replaces sensitive data with codes to pseudonymize the data, and otherwise ensures compliance with selected privacy settings and data security requirements and regulations.

In several example embodiments, the elements and teachings of the various illustrative example embodiments may be combined in whole or in part in some or all of the illustrative example embodiments. In addition, one or more of the elements and teachings of the various illustrative example embodiments may be omitted, at least in part, and/or combined, at least in part, with one or more of the other elements and teachings of the various illustrative embodiments.

Any spatial references such as, for example, "upper," "lower," "above," "below," "between," "bottom," "vertical," "horizontal," "angular," "upwards," "downwards," "side-to-side," "left-to-right," "right-to-left," "top-to-bottom," "bottom-to-top," "top," "bottom," "bottom-up," "top-down," etc., are for the purpose of illustration only and do not limit the specific orientation or location of the structure described above. Connection references, such as "attached," "coupled," "connected," and "joined" are to be construed broadly and may include intermediate members between a collection of elements and relative movement between elements unless otherwise indicated. As such, connection references do not necessarily imply that two elements are directly connected and in fixed relation to each other. The term "or" shall be interpreted to mean "and/or" rather than "exclusive or." Unless otherwise noted in the claims, stated values shall be interpreted as illustrative only and shall not be taken to be limiting.

Additionally, the phrase "at least one of A and B" should be understood to mean "A, B, or both A and B." The phrase "one or more of the following: A, B, and C" should be understood to mean "A, B, C, A and B, B and C, A and C, or all three of A, B, and C." The phrase "one or more of A, B, and C" should be understood to mean "A, B, C, A and B, B and C, A and C, or all three of A, B, and C."

Although several example embodiments have been described in detail above, the embodiments described are examples only and are not limiting, and those skilled in the art will readily appreciate that many other modifications, changes, and/or substitutions are possible in the example embodiments without materially departing from the novel teachings and advantages of the present disclosure. Accordingly, all such modifications, changes, and/or substitutions are intended to be included within the scope of this disclosure as defined in the following claims.

What is claimed is:

1. An adhesive carrier, comprising:
   a ring-shaped carrier body having a top edge opposite to a bottom edge;
   an adhesive sheet having an adhesive surface opposite to a non-adhesive surface, wherein the non-adhesive surface is bonded to the bottom edge of the ring-shaped carrier body, wherein an energy director feature protrudes away from the bottom edge through the non-adhesive surface, the adhesive sheet, and the adhesive surface, the energy director feature connecting the bottom edge and the adhesive sheet at an interface, wherein the interface between the bottom edge of the ring-shaped carrier body and the adhesive sheet comprises a thermally welded connection, wherein the energy director feature melts and integrates with the adhesive sheet; and
   a removable liner attached to the adhesive surface, wherein the removable liner extends beyond a perimeter of the adhesive sheet.

2. The adhesive carrier of claim 1, further comprising a monitoring device nested in the ring-shaped carrier body, such that the ring-shaped carrier body surrounds a sidewall of the monitoring device.

3. The adhesive carrier of claim 1, further comprising a monitoring device disposed over the ring-shaped carrier body, such that both the top edge and the bottom edge are under the monitoring device.

4. The adhesive carrier of claim 1, wherein the ring-shaped carrier body includes a plurality of ribbing structures that each extend from a top portion to a bottom portion along an interior surface of the ring-shaped carrier body.

5. The adhesive carrier of claim 4, wherein the ring-shaped carrier body has an elongated configuration, and wherein the plurality of ribbing structures are symmetrically positioned along the interior surface of the ring-shaped carrier body about a major axis and a minor axis of the ring-shaped carrier body, respectively, the major axis and the minor axis being perpendicular to each other.

6. The adhesive carrier of claim 1, wherein the ring-shaped carrier body includes a first stabilizer and a second stabilizer opposite to the first stabilizer, the first stabilizer and the second stabilizer being arranged along an axis of the ring-shaped carrier body, and wherein the first stabilizer and the second stabilizer are each oriented at an acute angle with respect to the top edge.

7. The adhesive carrier of claim 1, wherein the adhesive sheet includes an adhesive layer bonded to a non-adhesive backing layer, and wherein the ring-shaped carrier body is bonded to the non-adhesive backing layer of the adhesive sheet.

\* \* \* \* \*